United States Patent [19]

Horrobin

[11] Patent Number: 4,535,093

[45] Date of Patent: Aug. 13, 1985

[54] PHARMACEUTICAL AND DIETARY COMPOSITION

[75] Inventor: David F. Horrobin, Montreal, Canada

[73] Assignee: Efamol Limited, London, England

[21] Appl. No.: 476,708

[22] Filed: Mar. 18, 1983

Related U.S. Application Data

[62] Division of Ser. No. 150,402, May 15, 1980, Pat. No. 4,388,324.

[30] Foreign Application Priority Data

May 18, 1979 [GB] United Kingdom ............... 7917456

[51] Int. Cl.$^3$ .................... A01N 37/02; A01N 37/00
[52] U.S. Cl. ..................................... 514/560; 514/552
[58] Field of Search ................................ 424/312, 318

[56] References Cited

U.S. PATENT DOCUMENTS

| | | | |
|---|---|---|---|
| 3,676,472 | 7/1972 | Zilliken et al. | 424/318 |
| 3,953,499 | 4/1976 | Pike et al. | 560/121 |
| 3,993,775 | 11/1976 | Williams | 424/312 |
| 4,058,594 | 11/1977 | Williams | 424/318 |
| 4,388,324 | 6/1983 | Horrobin | 424/312 |

FOREIGN PATENT DOCUMENTS

| | | | |
|---|---|---|---|
| 0003407 | 6/1979 | European Pat. Off. | 424/318 |
| 2352797 | 4/1975 | Fed. Rep. of Germany | 424/318 |
| 2749492 | 5/1978 | Fed. Rep. of Germany | 424/318 |
| 1240513 | 7/1971 | France | 424/318 |

OTHER PUBLICATIONS

Kernoff, et al., British Med. Journal (1977), vol. 2, 1441-1444.

*Primary Examiner*—Delbert R. Phillips
*Attorney, Agent, or Firm*—Cushman, Darby & Cushman

[57] ABSTRACT

Composition and use of γ-linolenic acid and related materials with ascorbic acid, or ethyl alcohol, or an opiate antagonist such as naloxone, nalorphine or levallorphan, for treating alcoholism or moderating the effects of taking alcohol.

8 Claims, No Drawings

PHARMACEUTICAL AND DIETARY COMPOSITION

This is a division of U.S. application Ser. No. 150,402, filed May 15, 1980, now U.S. Pat. No. 4,388,324.

FIELD OF THE INVENTION

This invention relates to the treatment of certain diseases and disorders primarily, but no exclusively, in the field of human medicine and to compositions for use therein.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid, γ-linolenic acid (GLA) and dihomo-γ-linolenic acid (DGLA)

Conversion of these materials in the body is believed to be as shown in the following diagram:

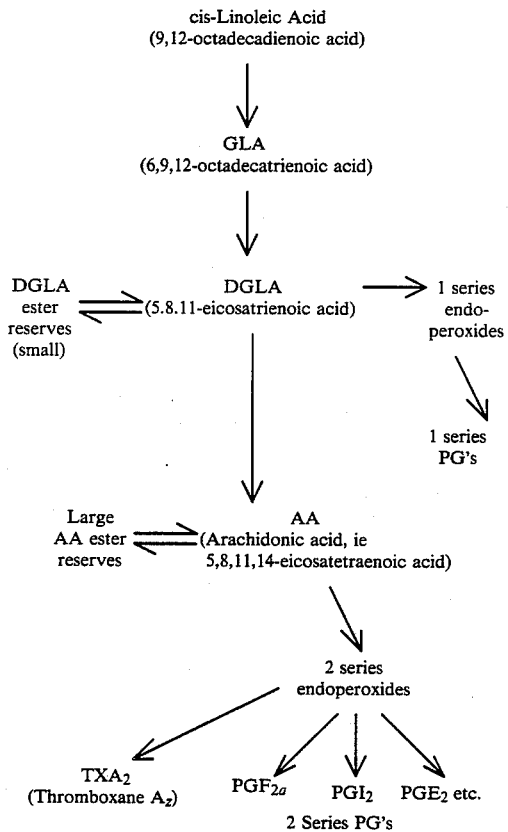

The broad outline of this pathway is well known, and it brings out clearly that a major function of essential fatty acids (EFAs) is to act as precursors for prostaglandins, 1 series PGs being formed from dihomo-γ-linolenic acid (DGLA) and 2 series PGs from arachidonic acid (AA). DGLA and AA are present in food in only small quantities, and the major EFA in food is linoleic acid which is first converted to γ-linolenic acid (GLA) and then to DGLA and AA. The conversion of linoleic acid to GLA is blocked by a high fat and high carbohydrate diet, by ageing and for example by diabetes. Stores of AA in the body in the form of lipid esters are very large indeed. In contrast only small amounts of DGLA ester are present.

INVENTION AND BACKGROUND

DGLA is the key substance. GLA is almost completely and very rapidly converted in the body to DGLA and so for practical purposes the oral administration of DGLA and GLA amounts to the same thing. DGLA can be converted to a storage form, changed to arachidonic acid and thence to PGs of the 2 series, or converted to PGs of the 1 series.

There is increasing evidence that PGs of the 1 series play a vital role in a number of key areas. First, PGE 1 activates T lymphocytes. Defective T lymphocytes are believed to be involved in causing a wide range of allergic and inflammatory disorders and in making individuals susceptible to cancer and infections of all types. Second, PGE 1 is important in preventing over-production of collagen and fibrous tissue, a factor which plays a major role in arthritis and the so-called collagen diseases. Third, PGE 1 levels are extremely low in patients with schizophrenia and are moderately low in patients with depression. Fourth, PGE 1 appears to be important in controlling cholesterol levels and necessary for the normal actions of insulin. Fifth, PGE 1 dilates blood vessels and may be expected to be helpful in any situation in which vessel spasm occurs. Sixth, PGE 1 appears to inhibit the production of 2-series PG's, levels of which are raised in a wide variety of inflammatory disorders. Seventh, PGE 1 increases production of cyclic AMP which has anti-inflammatory effects.

There are therefore very strong reasons, and this broadly is an aim of the present invention, for influencing the 1-series/2-series PG balance in the body in favour of 1-series PG's and specifically for selectivity enhancing formation of PGs of the 1-series and particularly PGE 1. The diseases and disorders below are among those in which such action is indicated:

1. Situations in which defective T lymphocyte function has been described such as allergic and inflammatory disorders, multiple sclerosis, and schizophrenia.
2. Situations in which regulation of collagen formation and breakdown is defective including rheumatoid arthritis, systemic lupus erythematosus, Crohn's disease and the various "collagen" diseases.
3. Mental illnesses in which low PGE 1 levels have been reported, including depression and schizophrenia. In depression, platelet PGE 1 production is moderately reduced whereas in schizophrenia it is severely reduced.
4. Disorders of lipid and carbohydrate metabolism in particular diabetes mellitus and situations in which blood cholesterol levels are elevated.
5. Disorders in which there is a tendency of blood vessels to go into spasm such as angina pectoris, myocardial infarction and Reynaud's syndrome.
6. Disorders of inflammation in which there may be excessive production of 2-series PGs from arachidonic acid, often coupled with low levels of cyclic AMP.

Selective enhancement of 1-series PG production has been explored in human platelets. The method is given in detail later herein but briefly human platelets are incubated with radioactive DGLA or arachidonic acid. The PGs produced during incubation are extracted by conventional means and separated by thin layer chromatography, and the amount of radioactivity appearing in each PG or related substance is counted. PGE 1, PGF 1α and thromboxane B1 from DGLA, and PGE 2, PGF 2α and thromboxane B2 from AA are estimated. The results, as given herein, demonstrate the inventor's belief that the effects of various agents on AA and DGLA conversion can be quite different and that it is possible to selectively enhance formation of PGE 1 and other 1-series PG compounds. The effect is believed to be by influencing the conversion of DGLA to the 1-series PGs.

The balance between 1-series and 2-series PGs is, the inventor believes, significant in terms of overall control of the conversion pathways given earlier. Such control is not understood in detail but without restriction to the theory it appears first that PGE 2 is able to enhance the formation of 1-series PG's, and second that PGE 1 is able to block arachidonic acid mobilisation from tissue stores. Thus the conditions for a negative feedback control loop exist; overproduction of PGE 2 from AA will activate PGE 1 synthesis, the PGE 1 will inhibit AA mobilisation, and production of 2-series PG's will drop. Further, TXA 2, an unstable product of the 2-series endoperoxides arising in 2-series PG production, also appears to enhance 1-series PG and in particular PGE 1 production. Thus again the activity of the 2-series PG synthesis pathway gives rise indirectly to a material that controls that pathway.

EFFECTIVE AGENTS

The inventor has tested the following agents for their effect on PG metabolism in the platelet system.

The agents, which can affect DGLA conversion at concentrations which have no effect on AA conversion, are:

1. Vitamin C, which at concentrations from 10 μg/ml to 1 mg/ml causes a dose dependent rise in formation of PGE 1.
2. Ethyl alcohol, which at concentrations from 30 to 300 mg% also causes a dose dependent rise in formation of PGE 1.
3. The opiate antagonist naloxone, which at 20 μg/ml, reverses an effect of 1-levorphanol at 100 μg/ml in inhibiting conversion of DGLA to PGE1. The d-isomer of levorphanol, which is devoid of opiate activity, had no such effect. The reversal indicates that activation of opiate receptors inhibits PGE1 formations and thus that endogenous opioids, and opioids formed in the gut from partial protein digestion, may inhibit PGE1 formation. This inhibition is reversed by opiate antagonists such as naloxone, desirable in situations where opiate excess is suspected such as schizophrenia, coeliac disease and psoriasis. It should be noted that an opiate action is by definition one activated by 1-but not by d-levorphanol and that an opiate antagonist is a material blocking this 1-levorphanol activation.

DETAILED DISCUSSION, VITAMIN C

In individuals who consume large amounts of vitamin C body stores of DGLA could become seriously depleted leading to a deficiency of PGE1 and DGLA.

The formation of endoperoxides in the conversion of AA and DLGA involves oxygen and it has been postulated that agents like vitamin C play a part in this so-called cyclo-oxygenase reaction. There are reports in the literature of high concentrations of vitamin C both enhancing and reducing PG formation, but in the inventor's belief no one has considered that any agent may have a selective action on the conversion of DGLA or of AA to endoperoxides and hence on to the formation of PGs. The inventor has found that the effect of vitamin C is in fact highly specific at physiological concentrations (e.g. up to 2 mg/ml). At these concentrations vitamin C has a substantial effect in enhancing formation of 1 series PGs, including PGE1, while having no significant effect on formation of 2 series PGs. Thus the combination of vitamin C with DGLA or GLA, an aspect of the invention, will specifically enhance formation of 1 series PGs without affecting conversion of AA to 2 series PGs. There is strong evidence that activation of this reaction is a major contributor to the physiological action of vitamin C, so that anyone taking vitamin C should also be ensuring that there are adequate levels of DGLA in the body.

ALCOHOL

The idea that ethyl alcohol may affect PG formation has several times been considered but not with specific reference to 1 or 2 series PGs. The main experimental evidence to date has related to conversion of AA and it has been demonstrated that extremely high levels of ethanol can block the formation of thromboxane B2. The relative effects of alcohol on AA and DGLA conversion have not been considered. The inventor has found that starting at the threshold 20–30 mg%, alcohol haas an effect on conversion of DGLA to 1 series PGs, greatly enhancing their production. There is no significant effect on conversion of AA to 2 series compounds until concentrations of above 300 mg% are reached when the effect is an inhibition of thromboxane B2 formation i.e. the opposite action to the effect of the 1 series.

This effect of alcohol can account for a number of its effects, particularly in relation to those on mood. It means that in those who consume large amounts of alcohol their is a considerable danger of depletion of DGLA stores and therefore of a failure of adequate PGE1 production following a period of excess PGE1 formation. This is a particular risk in alcoholics whose dietary intake of many foods is likely to be defective. There is therefore a strong case for ensuring that in those whose alcohol consumption is high, EFA intake should be such that body levels of DGLA are maintained.

In summary, alcohol over the range 30 to 300 mg% causes a marked enhancement of up to 60% in the amount of 14C-DGLA converted to PGE1. Up to 100 mg% alcohol has little effect on arachidonate metabolism but at 300 mg% it tends to inhibit conversion of arachidonate to PGs and particularly thromboxanes. The effects on the 1 and 2 series PGs are therefore opposite. The threshold of the effect is at about 20–30 mg% which is the concentration of alcohol in human plasma at which signs of mild intoxication first appear. 300 mg% is a concentration which produces "blind drunkenness."

Alcoholic intoxication will therefore enhance formation of PGE1 and deplete the limited body stores of DGLA. Post-intoxication depression which is such a major factor in the development of chronic alcoholism may well be related to a fall of PGE1 formation due to depletion of DGLA stores. The withdrawal syndrome in chronic alcoholics is often schizophrenia-like and may be caused by extremely severe DGLA depletion.

Further, there is evidence that depletion of PGE1 formation is associated with increased production of fibrous tissue, so that the development of liver cirrhosis in some chronic alcoholics may be related to chronic depletion of DGLA. Incidentally the stimulation of PGE1 formation by ethanol explains the reported desirable effects of modest consumption of alcohol (insufficient to deplete DGLA) such as prevention of heart attacks and resistance to viral infections.

Thus DGLA and materials giving it in the body (the "oil", see later) are of value in at least three ways.
1. In mild to moderate consumers of alcohol, to help prevent depletion of body stores of DGLA, post-intoxication depression and other short and long term features such as elevated cholesterol levels related to essential fatty acid deficiency.
2. In chronic alcoholics undergoing withdrawal, to replenish DGLA stores and maintain PGE1 formation, thus preventing the worst features of withdrawal.
3. In chronic continuing consumers of alcohol, to partially or completely avoid long term adverse effects such as cirrhosis of the liver.

OPIATE ANTAGONISTS

Morphine and related opiate drugs have actions on many tissues of the body. These actions are believed to be due to activation of a specific "receptor" which is chemically complementary to the drugs. The opiate receptor is identified in three main ways:
1. Morphine and drugs with a similar action activate it and produce a biological effect.
2. l-levorphanol binds to and activates the opiate receptor whereas its d-isomer does not. Effects which are produced by l-levorphanol and not by d-levorphanol are considered to be due to activation of the opiate receptor.
3. Certain compounds bind to the receptor but fail to activate it or only activate it partially. These compounds prevent the opiates activating the receptor and are therefore known as antagonists or, if they can weakly activate the receptor, as partial agonists/antagonists. The purest known antagonist is naloxone and drug actions which are blocked by naloxone are considered to be due to activation of opiate receptors.

Within the last five years it has become apparent that the opiate receptors exist because there are a series of natural compounds known as opioids, some of which are produced within the body and some of which are produced in the gut as a result of partial protein digestion. There is strong suggestive evidence that these compounds are involved in schizophrenia and possibly in other disorders such as coeliac disease and psoriasis.

Using human platelets the inventor has been able to demonstrate that l-levorphanol but not d-levorphanol is able to block the formation of 1 series PGs from DGLA without blocking the formation of 2 series PGs from AA. The effect of l-levorphanol can be blocked by naloxone. The natural opioid, $\beta$-endorphin, has an effect similar to levorphanol and this effect can also be reversed by naloxone.

Platelets from schizophrenics are known to produce very small amounts of PGE1 from DGLA: normal platelets treated with l-levorphanol or $\beta$-endorphin thus behave like schizophrenic platelets.

Thus:

1. Opiate drugs and opioids are able to block formation of PGE1. These effects can be reversed by opiate antagonists such as naloxone.
2. If one wants to ensure maximum formation of 1 series PGs from DGLA, especially in situations in which there may be endogenous opioids, DGLA should therefore be administered in conjunction with opiate antagonists such as naloxone.

The studies suggest that in diseases where there is overactivity of an opioid at some site, then opiate antagonists oppose this action and enhance the conversion of DGLA to PGE1. Such overactivity may be produced by excess amounts of a normal opioid, the presence of an abnormal opioid, or abnormal tissue sensitivity to normal opioid levels. It is of interest that a natural defect of conversion of DGLA to PGE1 in schizophrenic platelets can be limited in normal platelets by incubation with l-levorphanol.

Therefore, in conditions in which it is desirable to increase formation of PGE1 by increasing intake of DGLA, GLA or their precursors, the effect is enhanced by opiate antagonists in situations where there is an excess of endogenous opioid activity. Examples of such conditions include schizophrenia and coeliac disease. Opiate antagonists known per se and used clinically include nalorphine, levallorphan and naloxone but there is no restriction to these for use in the present invention. Naloxone, as a pure antagonist, is preferred.

MATERIALS AND METHODS

The detailed technique with platelets is given below by way of example.

$(1\text{-}^{14}C)$ arachidonic acid and $(1\text{-}^{14}C)$ dihomo-$\gamma$-linolenic acid were used, diluted with hexane to specific activities of about 5 $\mu Ci/\mu mol$. One day expired (2 days old) human platelets were obtained and used within 48 hours of expiration. One unit was centrifuged at 1000 g for 15 minutes and the supernatant drawn off. The platelet pellet was resuspended in Tris-NaCl-EDTA buffer, made up of 0.15M NaCl, 0.15M Tris HCl at pH 7.4 and 0.077M NaEDTA (90:8:2 v/v/v). The platelets were recentrifuged, the supernatant removed and the pellet resuspended in Krebs-Henseleit buffer (without calcium) at pH 7.4 The washed platelet suspension contained about 1–2% red blood cells. All glassware used in the preparation of the platelets was siliconized.

Four equal sized 1 ml aliquots of the platelet suspension, containing $10^9$ platelets/ml were incubated with e.g. 0.5 $\mu Ci$ $^{14}C$-DGLA for five minutes. At the beginning of the incubation the material under test was added to the suspensions. The reaction was stopped after five minutes by addition of 1/10 volume of 10% formic acid. The suspension was then extracted three times with ethyl acetate and the fractions pooled and dried under vacuum. The extract was then taken up with 5 ml chloroform/methanol (2/1, v/v). Recovery of radioactive material in the extract was checked by taking 50 $\mu l$ of the chloroform/methanol and counting by liquid scintillation. Recovery was in the range 80–95% in most experiments.

The chloroform/methanol extract was then reduced in volume to 1 ml under dry prepurified nitrogen. Thin layer chromatography was carried out on 500 $\mu g$ precoated, prescored silica gel G Uniplates (Analtech). Plates were activated by heating to 100° C. for 1 hour immediately prior to use. The solvent system was chloroform:methanol:acetic acid:water (90:8:1:0.8). Reference compounds (PGsE1 and F1$\alpha$ and thromboxane B1)

were run at the same time and visualised by phosphomolybdic acid spray followed by brief heating. The bands on the plates corresponding to the reference PGE1, PFG1α and TXB1 were scraped off and eluted with 20 ml acetone. Each elution was then evaporated to dryness and counted by liquid scintillation (Beckman 100 LS counter).

Using the same batch of platelets at the same time exactly similar experiments wre carried out with $^{14}$C-AA amd PGE2, PGE2α and TXB2 as reference compounds. Three experiments were performed with DGLA and three with AA.

RELATIONSHIP TO PREVIOUS PROPOSALS

The above approaches may be used in combination with other materials as disclosed in the earlier patent applications of the inventor namely European Nos. 79300079.5 and 79300546.3 (Publication Nos. 0 003 407 and 0 004 770; U.S. Ser. Nos. 004,924 and 029,058).

Among these materials are a number believed to act by enhancing mobilisation of DGLA reserves, including zinc, penicillin and β-lactam antibiotics generally, and also penicillamine, phenformin and levamisole when the other effects of these materials are acceptable.

Further, since there is evidence that thromboxane A2 may indirectly enhance formation of PGE 1, substances such as colchicine, amantadine and melatonin, and also griseofulvin, vinblastine, vincristine and interferon as discussed in the pending patent applications and believed to act through increasing the production or effect of thromboxane A2, can also be used in conjunction with the materials of the present invention.

As appears from the earlier patent applications, in searching for ways to regulate PGE1 formation the inventor has previously concentrated on the conversion of DGLA stores to free DGLA since this is belived to be a key rate-limiting step and since it has also been believed that factors which regulate conversion of free arachidonate to PGs will also regulate conversion of free DGLA to PGs. The present work has been more on the conversion of DGLA and of AA to the respective PGs, and as noted above it has been found that the factors regulating the two PG pathways are in some respects quite different. The discoveries on which the present application is based however build on and add to the earlier inventions rather than superseding them.

THE PRESENT INVENTION

In the light of the general discussion above the present invention in its various aspects may be summarised as:

A. A method of treating alcoholism or moderating the effects of taking alcohol which comprises administering an effective amount of γ-linolenic acid and/or dihomo-γ-linolenic acid, optionally in association with linoleic and if desired other fat acids, said acids being used if desired as physiologically functional derivatives thereof.

B. A pharmaceutical composition specifically therefor, comprising γ-linolenic acid and/or dihomo-γ-linolenic acid, as above, alone or in an acceptable pharmaceutical vehicle.

C. A method of moderating the effects of taking alcohol or of treating alcoholism which comprises administering an effective amount of γ-linolenic acid or other material as above, in conjunction with (a) an effective amount of a material enhancing physiological conversion of DGLA to 1 series PGs, and in particular PGE1, without at the same time substantially enhancing synthesis of 2 series PGs, or specifically, (b) an effective amount of one or more materials selected from ascorbic acid, ethyl alcohol, and opiate antagonists.

D. A pharmaceutical composition per se, comprising γ-linolenic acid or other material as above in conjunction with said material (a) or (b), alone or in an acceptable pharmaceutical vehicle.

E. A method as C, comprising further administering an effective amount of (c) a material enhancing physiological synthesis of 1 series PGs, and in particular PGE1, by mobilisation of DGLA reserves, or of (d), specifically, zinc, a β-lactam antibiotic as described herein, penicillamine, lavamisole or phenformin.

F. A pharmaceutical composition per se, as D, further comprising said material (c) or (d), alone or in an acceptable pharmaceutical vehicle.

G. A method as C comprising further administering an effective amount of (e) a material enhancing production or effect of thromboxane A2, or of (F) specifically, melatonin or colchicine or amantadine.

H. A pharmaceutical composition per se as D, further comprising said material (e) or (f), alone or in an acceptable pharmaceutical vehicle.

DOSE RANGES

Dose ranges for ascorbic acid, opiate antagonists and alcohol in humans are as follows:

| | |
|---|---|
| Ascorbic acid | outer limits 50 mg to 50 g per day |
| | desirable dose 250 mg to 5 g per day |
| Naloxone | outer limits 0.1 to 500 mg/day for example orally or parenterally in four or six divided doses |
| | desirable dose 10 mg to 200 mg/day |
| Nalorphine | outer limits 1 mg to 5 g/day for example in divided doses orally or parenterally |
| | desirable dose 10 mg to 2 g/day |
| Levallorphan | outer limits 0.2 mg to 1 g/day for example in divided doses given orally or parenterally |
| Alcohol | outer limits 5 to 500 ml/day |
| | desirable dose 50 to 200 ml/day |

Dose ranges for materials auxiliary to those of the invention are discussed elsewhere herein. All the materials may be given in doses of for example one half, one third or one quarter of the above amounts. The amounts are related to those quoted earlier for platelet and other experiments, though of course a precise relation cannot be given in view of variation in inactivation and excretion rates and volume of distribution.

PACKS

If it is not desired to have compositions comprising the active materials together, as listed above, packs may be prepared comprising the materials presented for separate or part joint and part separate administration in the appropriate relative amounts, and such packs are within the purview of the invention.

DIETARY COMPOSITIONS

The invention is chiefly described in terms of pharmaceutical compositions, but it will be understood that the γ-linolenic and other acids, being in the nature of dietary supplements, could be incorporated in a dietary margarine or other foodstuffs; such foodstuffs, possibly containing other active materials and generally referred to in this description as dietary or pharmaceutical compositions, are within the purview of the invention and thus of the term pharmaceutical compositions, packs or the like used in the claims.

VETERINARY APPLICATIONS

It will be understood that where a disorder of a kind calling for treatment in animals arises, the invention while described primarily in terms of human medicine and treatment is equally applicable in the veterinary field.

AMOUNTS OF ACTIVE MATERIALS (ADJUNCTS TO PRESENT INVENTION)

Amount of materials are:

| | |
|---|---|
| Zinc | 2.5 to 800 mg/day, preferably 10–80 mg calculated as zinc |
| β-lactam antibiotics | 0.5 to 10 g/day |
| Penicillamine | 50 mg to 10 g/day |
| Phenformin | 10 mg to 5 g/day |
| Levamisole | 10 mg to 2 g/day |
| Colchicine | 0.3 to 15 mg/day, preferably 0.6 to 2.4 mg |
| Melatonin | 10 mg to 5 g/day |
| Amantadine | 100 mg to 1000 mg/day |
| Griseofulvin | 0.5 to 5 g/day |
| Vinblastine | 0.5 to 5 mg/kg/week (average weight 70 kg) |
| Vincristine | 0.1 to 1.0 mg/kg/week (average weight 70 kg) |
| Interferon (by injection) | $1 \times 10^5$ to $1 \times 10^8$ units/day |

Detailed discussion of suitable amounts and forms of use is contained in the published patent applications referred to earlier, to which reference may be made. In particular the β-lactam antibiotics are conveniently any of the known penicillin and cephalosporin antibiotics (including semi-synthetic antibiotics) such as, for example, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts e.g. sodium and potassium salts, and salts with organic bases, and reference to an antibiotic herein includes reference to such derivatives.

AMOUNTS OF γ-LINOLENIC AND OTHER ACIDS SPECIFICALLY

A preferred daily dosage for all purposes for an adult (weight ca 75 kg) is from 0.05 to 0.1 up to 1, 2, 5 or even 10 g as required of γ-linolenic acid or equivalent weight calculated as γ-linolenic acid or a physiologically functional derivative thereof. Amounts in particular may be 0.1 to 1.0 g daily. Corresponding doses of the Oenothera oil containing 8 to 10% of γ-linolenic acid, are easily calculated. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3 or 4 subdivisions thereof as convenient.

FORMS AND SOURCES OF γ-LINOLENIC AND OTHER ACIDS

Convenient physiologically functional derivatives of γ-linolenic acid and dihomo-γ-linolenic acid for use according to the invention for all the purposes described include the $C_1$–$C_4$ alkyl (e.g. methyl) esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof), as such, with an acceptable pharmaceutical vehicle. It is at present convenient to incorporate the γ-linolenic acid into compositions in the form of an available oil having a high γ-linolenic acid content, hence references to "oil" herein.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linolenic acid (about 72%) in the form of their glycerides together with other glycerides (percentages based on total fatty acids). Other sources of γ-linolenic acid are Borage species such as *Borago officinalis* which, though current yield per acre is low, provide a richer source of γ-linolenic acid than Oenothera oil. Recent studies on fungi which can be cultivated by fermentation promise a fungal oil source.

The seed oil extracts referred to above can be used as such or can for example if desired be fractionated to yield an oily composition containing the triglycerides of γ-linolenic and linoleic as the main fatty acid components, the γ-linolenic acid content being if desired a major proportion. Seed oil extracts appear to have a stabilising effect upon any dihomo-γ-linolenic acid or physiologically functional derivative thereof.

PHARMACEUTICAL PRESENTATION

The compositions according to the invention are conveniently in a form suitable for oral, rectal, parenteral or topical administration in a suitable pharmaceutical vehicle, as discussed in detail for example in Williams U.K. Patent Specification No. 1 082 624, to which reference may be made, and in any case very well known generally for any particular kind of preparation. Thus for example tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate pharmaceutical compositions useful in treating according to the invention:

EXAMPLES

Pharmaceutical compositions contain a unit dose of an oil extract from the seeds of *Oenothera biennis L.*, and of one of the active materials of the present invention, optionally with methyl dihomo-γ-linolenate and/or zinc oleate and/or penicillin V and/or any of the other active materials referred to herein directly or by cross reference to other patent applications of the inventor. They may be presented by encapsulation of the natural oil in soft gelatin capsules by known methods.

The oil is extracted from the seeds by one of the conventional methods of extraction such as cold pressure, screw pressure after partially cooking the seeds, or solvent extraction.

Fractionation of a typical sample of this oil shows a yield of 97.0% oil in the form of methyl esters, with the relative proportions:

| Palmitate | 6.15 |
|---|---|
| Stearate | 1.6 |
| Oleate | 10.15 |
| Linoleate | 72.6 |
| γ-Linolenate | 8.9 |

As preservative, α-tocopherol is added to the oil in a concentration of 0.1%.

Gelatin capsules containing oil extracts prepared as described above, each having the following contents of active ingredients (0.5 g oil extract=ca 0.045 g γ-linolenic acid), are prepared in conventional fashion.

The following are specific examples of capsules that may be given, two capsules three times a day, in treatment of the conditions listed earlier.

EXAMPLE 1

| Oil extract | 0.5 g |
|---|---|
| Zinc sulphate | 10 mg |

Two capsules may be administered thrice daily in the treatment of alcoholism, giving a daily dose of γ-linolenic acid of ca. 0.27 g. Capsules without zinc are an alternative. Zinc oleate 20 mg is an alternative to zinc sulphate.

EXAMPLES 2(a)-2(e)

Similarly to Example 1 the following may be administered:

| (a) | Oil extract | 0.5 g |
|---|---|---|
| | Methyl dihomo-γ-linolenate | 10 mg |
| | Zinc sulphate | 20 mg |
| (b) | Oil extract | 0.5 g |
| | Penicillin V | 0.25 g |

(Levamisole 25 mg, penicillamine 100 mg or phenformin 25 mg are alternatives to penicillin here and in (c) and (d) below).

| (c) | Oil extract | 0.5 g |
|---|---|---|
| | Penicillin V | 0.25 g |
| | Zinc sulphate | 10 mg |
| (d) | Oil extract | 0.5 g |
| | Methyl dihomo-γ-linolenate | 10 mg |
| | Penicilln V | 0.25 g |
| | Zinc sulphate | 10 mg |
| (e) | Oil extract | 0.5 g |
| | Methyl dihomo-γ-linolenate | 10 mg |

EXAMPLE 3

The treatment of disorders with γ-linolenic acid or equivalent in combination with ethyl alcohol, as described earlier may be carried out by giving the materials of Examples 1 and 2 as there set out with the alcohol in any convenient form to give 30 to 300 mg% alcohol in the body.

EXAMPLES 4 to 10

The treatment of disorders with ascorbic acid or opiate antagonists, as described earlier, may be carried out by giving the following in the way set out in Example 1:

| 4. | Oil extract | 0.5 g |
|---|---|---|
| | Ascorbic acid | 100 mg |
| | Zinc sulphate | 10 mg |
| 5. | Oil extract | 0.5 g |
| | Ascorbic acid | 100 mg |
| | Colchicine | 0.2 mg |
| | Zinc sulphate | 10 mg |
| 6. | Oil extract | 0.5 g |
| | Ascorbic acid | 100 mg |
| | Colchicine | 0.2 mg |
| | Penicillin V | 250 mg |
| 7. | Oil extract | 0.5 g |
| | Ascorbic acid | 200 mg |
| | Naloxone | 5 mg |
| 8. | Oil extract | 0.5 g |
| | Zinc sulphate | 10 mg |
| | Naloxone | 5 mg |
| 9. | Oil extract | 0.5 g |
| | Zinc sulphate | 10 mg |
| | Nalorphine | 5 mg |
| 10. | Oil extract | 0.5 g |
| | Zinc sulphate | 10 mg |
| | Levallorphan | 5 mg |
| | Colchicine | 0.2 mg |

It will be understood throughout that while a full theoretical discussion of what is believed to be the reason for the effectiveness of the compositions proposed is given to aid understanding, the invention is in no way to be limited by this discussion.

VALUE OF OIL+VITAMIN C

A not uncommon condition, particularly in the elderly, is the sicca syndrome of lacrimal and salivary failure which, when coupled with connective tissue disease and in particular rheumatoid arthritis, is known as Sjögren's syndrome. The function of T lymphocytes is also impaired. No treatment has been known to increase tear and saliva flow, and lubricant drops and mouthwashes have to be resorted to, often as frequently as several times an hour.

The inventor's belief is that impaired PGE1 production is at the bottom of the difficulties and has found that in the NZB/W mouse, the animal model for SJögren's syndrome, γ-linolenic acid, as a precursor for PGE1, or PGE1 itself, can correct many of the immunological abnormalities of the strain. Moreover in the platelet system already referred to, the following changes in formation of products of DGLA metabolism were found at physiological levels of Vitamin C, there being no change in production of the corresponding AA metabolism products.

| | Ascorbate level | | |
|---|---|---|---|
| Product level % | 10 μg/ml | 33 μg/ml | 100 μg/ml |
| TXB1 | 130 | 147 | 171 |
| PGE1 | 134 | 144 | 184 |
| PGF1α | 107 | 123 | 150 |

Control = 100%; 10 μg/ml ascorbate = $5.7 \times 10^{-5}$ M.

The inventor has therefore conducted a small-scale human trial.

The first patient was a 52 year old woman with a history of classic moderate rheumatoid arthritis of three years duration. She also had a three-year history of dry mouth and dry eyes necessitating use of lubricant eye drops. Associated with these disorders were brittle, frequently cracking nails and hypersensitivity of the hands to soaps and detergents. This patient had been on high dose (7.5 g/day) vitamin C for a year. This had produced a subjective sense of well-being and some slight improvement in the dry eyes and mouth. 50 mg/day pyridoxine (desirable for normal EFA metabolism) and 6×0.6 ml Evening Primrose oil capsules per day were added to the regime. One month later eyes and mouth were normal, nail quality had substantially improved and the patient could expose her hands to soaps and detergents without adverse effects.

Four other patients with long-established Sjögren's syndrome have been tried on this regime and in all four there has been substantial improvement in tear and saliva production. One of these four was a patient who had developed the syndrome while taking practolo.

VALUE OF OIL+ETHANOL

The following results were obtained by the platelet techniques given in detail earlier:

| Alcohol (ethanol) concentration mg/100 ml | 0 | 33 | 100 | 300 |
|---|---|---|---|---|
| DGLA conversion to PGE1, PGF1 and TXB1 (total as % of control) | 100 | 160 | 200 | 230 |
| AA conversion to PGE2, PGF2 and TXB2 (total as % of control) | 100 | 110 | 90 | 100 |

The variation in the figures for AA conversion is not significant, but that for DGLA conversion shows a dose-related and substantial rise at these physiological ethanol concentrations, with the significance for PG metabolism and treatment of the effects of taking alcohol already discussed at length herein.

VALUE OF OIL+OPIATE ANTAGONISTS

In the platelet system l-levorphanol reduced formation of 1-series PGs, an effect abolished by naloxone and not shown by d-levorphanol. The concentrations concerned had no effect on production of 2-series PGs from AA. Thus if the levels of l-levorphanol used correspond to levels of natural opiates that are undesirably high, in which natural 1-series PG production may be expected to be suppressed, use of naloxone may be expected to assist.

In the table below results are expressed as percentages of control counts obtained without the drug and are the mean of three determinations:

| Amount of l-levorphanol | PGE1 | TXB1 |
|---|---|---|
| | (precursor DGLA) | |
| 18 ng/ml | 23% | 20% |

| Amount of l-levorphanol | PGE1 | TXB1 |
|---|---|---|
| | (precursor DGLA) | |
| 18 µg/ml | 72% | 76% |

It will be noted that an increased amount of l-levorphanol showed a reduced suppression effect. Such figures are frequently seen in PG work, higher concentrations showing a reduced or even reverse effect to lower concentrations.

I claim:

1. A pharmaceutical composition for treating alcoholism or moderating the effects of taking alcohol, comprising γ-linolenic acid and/or dihomo-γ-linolenic acid, as such or as a physiologically functional ester or other derivative thereof, in combination with ethyl alcohol, said composition being presented for administration in doses comprising 50 mg to 10 g of said γ-linolenic acid or dihomo-γ-linolenic acid or derivative (calculated as γ-linolenic acid) together with 5 to 500 ml of ethyl alcohol or one-half, one-third or one-quarter of said amounts.

2. A composition according to claim 1 comprising a further material influencing the 1-series/2-series PG balance in the body in favor of 1-series PGs by enhancing conversion of DGLA ester stores to free DGLA.

3. A composition according to claim 1 comprising further a physiologically assimilable zinc compound, or penicillamine, phenformin or levamisole, or a penicillin, cephalosporin or other γ-lactam antibiotic.

4. A composition according to claim 3 in dosage unit form comprising:

| Said zinc compound | 2.5 to 800 mg/day calculated zinc, or |
|---|---|
| β-lactam antibiotics | 0.5 to 10 g/day, or |
| Penicillamine | 50 mg to 10 g/day, or |
| Phenformin | 10 mg to 5 g/day, or |
| Levamisole | 10 mg to 2 g/day. |

5. A composition according to claim 1, comprising a further material influencing the 1-series/2-series PG balance in the body of favor of 1-series PGs by enhancing the physiological production or effect of TXA2.

6. A composition according to claim 1 comprising further colchicine, amantadine, melatonin, griseofulvin, vinblastine, vincristine, or interferon.

7. A composition according to claim 6 in dosage unit form comprising:

| Colchicine | 0.3 to 15 mg/day, or |
|---|---|
| Melatonin | 10 mg to 5 g/day, or |
| Amantadine | 100 mg to 1000 mg/day, or |
| Griseofulvin | 0.5 to 5 g/day, or |
| Vinblastine | 0.5 to 5 mg/kg/week, or |
| Vincristine | 0.1 to 1.0 mg/kg/week, or |
| Interferon | $1 \times 10^5$ to $1 \times 10^8$ units/day. |

8. A method of treating alcoholism is moderating the effects of taking alcohol which comprises administering an effective amount of γ-linolenic acid and/or dihomo-γ-linolenic acid, as such or as physiologically functional ester or other derivative thereof, in the form of a composition according to claim 1.

* * * * *